United States Patent

Langhals et al.

[11] Patent Number: 5,886,183
[45] Date of Patent: Mar. 23, 1999

[54] NAPHTHALENELACTAMIMIDE FLUORESCENCE DYES

[75] Inventors: Heinz Langhals, Ottobrunn; Petra Christa von Unold, München, both of Germany

[73] Assignee: Ciba Specialty Chemicals Corporatoin

[21] Appl. No.: 729,124

[22] Filed: Oct. 11, 1996

[30] Foreign Application Priority Data

Oct. 12, 1995 [CH] Switzerland .......................... 02882/95

[51] Int. Cl.[6] ...................... C07D 221/00; C07D 471/02
[52] U.S. Cl. ................... 546/62; 546/61; 546/26
[58] Field of Search ........................... 546/61, 62

[56] References Cited

FOREIGN PATENT DOCUMENTS 1495296  12/1977  United Kingdom .

OTHER PUBLICATIONS

E. F. Bondarenko et al., J. Org. Chem. USSR, 22(6), 1155 (1986).
Derwent Abstract, 79–46710B (Russian Patent SU 559,557).
Dalvi et al., Indian Journal of Chemistry, vol. 24B, pp. 377–382 (1985).
Chemical Abstracts, vol. 107, No. 5, (1987) 79–46710B.
Langhals et al., An gew. Chem. Int. Ed. Engl. 34, No. 20 (1995), pp. 2234–2236.
Hsu et al., Synthetic Communications, 19(11 & 12) pp. 1885–1889 (1989).
Nelsen, J. Amer. Chem. Soc. 89, 5925 (1967).
G.M Kheifets et al., J. Org. Chem. USSR, 13(2) pp. 1159–1164 (1977).

*Primary Examiner*—José G. Dees
*Assistant Examiner*—Sabiha N. Qazi
*Attorney, Agent, or Firm*—Kevin T. Mansfield; Jacob M. Levine

[57] ABSTRACT

Naphthalenelactamimides of the formula I

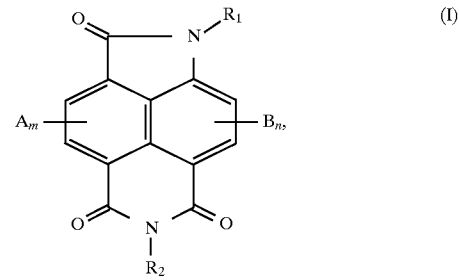

in which, for example, $R_1$ and $R_2$ are 2,5-di-tert-butylphenyl and m and n are 0, are novel dyes which have the distinctive features of pronounced fluorescence as a solid and in solvents and a good light-fastness. They are therefore suitable, for example, for mass dyeing of high molecular weight organic material, as laser dyes and for the preparation of printing toners, colour filters, organic photoreceptors, electroluminescent and photoluminescent elements, optical information storage media or solar collectors. The compounds of the the formula I can be prepared by reaction of the corresponding naphthalenetetracarboxylic acid bisimides with a base.

6 Claims, No Drawings

NAPHTHALENELACTAMIMIDE FLUORESCENCE DYES

The present invention relates to novel naphthalenelactamimides, a process for their preparation from the corresponding naphthalenetetracarboxylic acid bisimides, the bisimides and the related aminonaphthalenetricarboxylic acid imides as such, and to the use of the said compounds, for example for dyeing high molecular weight organic material.

Perylene-3,4:9,10-tetracarboxylic acid bisimides (1) are known as highly stable fluorescence dyes. In the case of the low homologues, the naphthalene-1,8: 4,5-tetracarboxylic acid bisimides (2), the absorption is shifted so far to the short wavelength region ($\lambda$=380 nm) that the substances are colourless or only just pale yellow, so that they can no longer be employed as a dye (the pale orange to pink colour shades described in the literature are to be attributed to contamination by perylene dyes). On the other hand, it would be of interest to have available fluorescence dyes with imide structures based on naphthalene, since naphthalene derivatives in general are easier to synthesize and to purify than perylene derivatives.

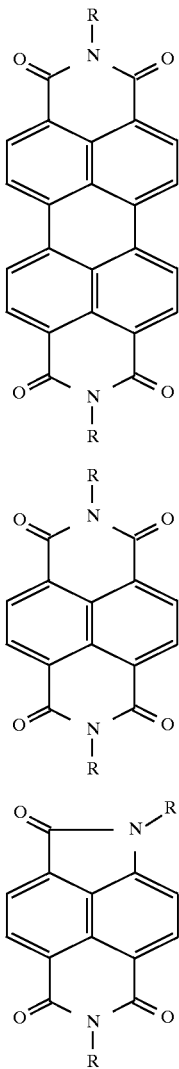

If the naphthalenetetracarboxylic acid bisimides are treated with KOH in alcohols, an astonishing ring-narrowing reaction is observed, $CO_2$ being split off, to form the naphthalene-imido-lactams 3. The formation of 3 using certain solvents has already been reported in J. Org. Chem. USSR, 22(6), 1155 (1986) and in SU Patent 559,557 (Derwent Abstract 46710B/25), and derivatives where R=CH$_3$, —CH$_2$CH$_2$CH$_2$OCH$_3$, C$_6$H$_5$ or 4-BrC$_6$H$_4$ have been prepared. However, these few compounds which have already been described are not known as fluorescent.

Naphthalenelactamimides substitued only on the imide nitrogen, in which the substituent is ethyl, phenyl, 4-methoxyphenyl, 3-chlorophenyl, 3-chloro-6-methoxyphenyl or 2,5-dichloro-phenyl, are known from Ind. J. Chem. 24B, 377–382 (1985), and are described therein as disperse dyes. These compounds also display no fluorescence.

The present invention relates to naphthalenelactamimides of the formula I

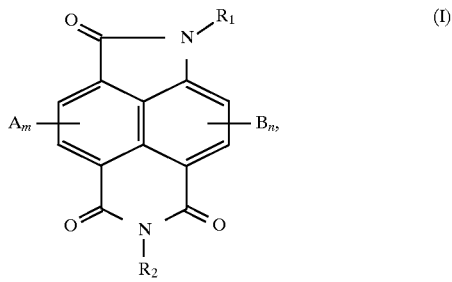

in which $R_1$ and $R_2$ independently of one another are $C_2$–$C_{25}$alkyl, where the alkyl group is unsubstituted or substituted by halogen, $C_6$–$C_{10}$aryl, $C_5$–$C_{10}$heteroaryl, or $C_3$–$C_{10}$cycloalkyl; $C_3$–$C_{10}$cycloalkyl or a radical of the formula II to IV

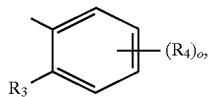

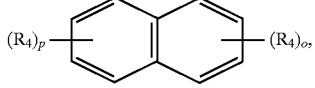

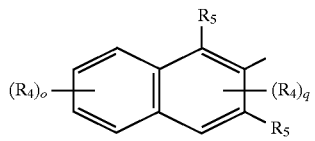

A and B independently of one another are $C_1$–$C_6$alkyl, $C_3$–$C_6$cycloalkyl, $C_6$–$C_{10}$aryl, halogen, cyano, nitro, —OR$_6$, —COR$_6$, —COOR$_6$, —OCOR$_6$, —CONR$_6$R$_7$, —OCONR$_6$R$_7$, —NR$_6$R$_7$, —NR$_6$COR$_7$, —NR$_6$COOR$_7$, —NR$_6$SO$_2$R$_7$, —SO$_2$R$_7$, —SO$_3$R$_7$, —SO$_2$NR$_6$R$_7$ or —N$\alpha$N—R$_6$, $R_3$ to $R_5$ independently of one another are halogen, $C_1$–$C_{12}$alkyl, phenyl or tolyl, where one $R_5$ can also be hydrogen, $R_6$ and $R_7$ independently of one another are $C_1$—$C_4$alkyl, phenyl or 4-tolyl, n and m independently of one another are 0, 1 or 2, o is an integer from 0 to 4, p is an integer from 0 to 3 and q is 0 or 1.

$C_2$–$C_{25}$alkyl $R_1$ and $R_2$ are straight-chain or, preferably, branched alkyl radicals. 2-Butyl, 2-methyl-2-butylhexyl, 2,2-dimethylheptyl or 2,2-dihexyloctyl, for example, are preferred. Alkyl substituted by cyclohexyl is, for example, 1-ethylcyclohexylmethyl or 1-n-propyl-cyclohexylmethyl, and alkyl substituted by aryl is, for example, 2-ethyl-2-phenylbutyl or 2-n-butyl-2-phenylhexyl.

$C_6$–$C_{10}$Aryl is, for example, phenyl which is unsubstituted or substituted by $C_1$–$C_4$alkyl, and naphthyl or biphenyl.

$C_5$–$C_{10}$Heteroaryl is a heterocyclic aromatic radical having 1, 2 or 3 hetero atoms, in particular N, O or S atoms, in the ring and, if appropriate, a fused-on benzene ring. Furyl, thienyl, pyrrolyl, imidazolyl, pyrazolyl, isothiazolyl, isoxazolyl, pyridyl, pyrazinyl, pyrimidyl, pyrazinyl, indolyl, isoindolyl, indazolyl, quinolyl, isoquinolyl, quinazolyl or carbazolyl, for example, are suitable.

$C_3$–$C_{10}$Cycloalkyl can be mono- or also polycyclic and is, for example, cyclopropyl, cyclobutyl, cyclopentyl, cyclohexyl, cyclooctyl, cyclodecyl, bicycloheptyl, bicyclooctyl or decalinyl.

$C_1$–$C_6$Alkyl is, for example, methyl, ethyl, n-propyl, isopropyl, n-butyl, sec-butyl, tert-butyl, pentyl, tert-amyl or hexyl, and $C_1$–$C_{12}$alkyl is additionally also, for example, octyl, 2,2-dimethylhexyl, decyl or dodecyl.

Halogen is, for example, bromine, fluorine and, in particular, chlorine.

Particularly suitable radicals $R_1$ and $R_2$ of the formula II are, for example, 2,3-dimethyl-phenyl, 2,5-dimethylphenyl, 2-methyl-5-tert-butylphenyl, 2-tert-butylphenyl, 2,3-di-tert-butylphenyl or 2,5-di-tert.-butylphenyl.

The compounds of the formula I according to the invention can be prepared, for example, by reaction of naphthalenetetracarboxylic acid bisimides of the formula V

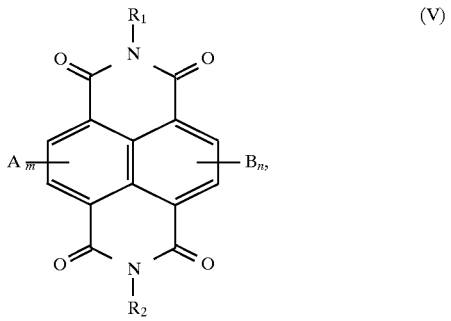

with a base.

The reaction is advantageously carried out in an organic solvent, preferably in methanol or ethanol. An alkali metal hydroxide, in particular potassium hydroxide, is preferably used as the base. The presence of an oxidizing agent, preferably oxygen, promotes the reaction. It is also of advantage if the solvent comprises dimethyl sulfoxide, advantgeously 30–50% by volume. The reaction preferably takes place at elevated temperature, in particular between 60° and 120° C.

It has been found that the abovementioned reaction takes place quite generally with aromatic bisimides, especially if the abovementioned preferred conditions are used.

Naphthalenetetracarboxylic acid bisimides of the formula V are likewise novel compounds and the present invention relates to these, as well as the 1-aminonaphthalenetricarboxylic acid derivatives of the formula VI formed as intermediates, in which $R_1$, $R_2$, A, B, m and n are as defined above and
M represents hydrogen or an alkali metal cation, in particular hydrogen or potassium, with the proviso that in compounds of the formula V, $R_1$ and $R_2$ are not both ethyl or decyl.

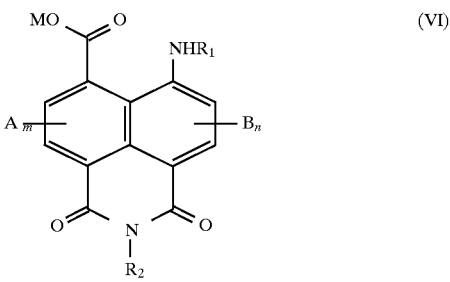

The naphthalenetetracarboxylic acid bisimides of the formula V can be prepared in a known manner, for example by reaction of the bisanhydride with the corresponding amine. Individual naphthalenetetracarboxylic acid bisimides which differ from the compounds of the formula V according to the invention are known from J. Amer. Chem. Soc. 89, 5925 (1967), Synth. Commun. 19,1885 (1989) and J. Org. Chem. USSR 13,1159 (1977).

If 2 is treated with KOH in ethanol, the reaction to give 3 surprisingly becomes the main reaction. Replacing ethanol by methanol and adding DMSO to the reaction mixture surprisingly increases the yield of 3 still further—in the case of aromatic substituents R, 3 is obtained in high yields, and in the case of aliphatic substituents, the yields are somewhat smaller but entirely acceptable.

To prepare 3, a reaction procedure in the presence of atmospheric oxygen is favourable, but the reaction can also be carried out without oxygen. A stable, extremely oxygen-sensitive reddish violet colouration (broad, unstructured absorption at 542 nm in a mixture of 2 ml of ethanol, 1 ml of DMSO and 0.2 g of KOH) of the reaction solution is then initially obtained, and during customary working up, in addition to 3 as the reaction product, a small amount of the hydrolysis product of an imide ring and unreacted starting material are also obtained.

A bathochromic shift in the absorption of 3 with respect to 2 into the visible range is observed, so that in contrast to 2, the substances can be used particularly well as dyes for the visible range.

If bisimides of the formula V are employed as starting substances, an intense fluorescence of the dyes of the formula I in solution and an intense fluorescence as solids are surprisingly found. The compounds of the formula I according to the invention furthermore have the distinctive feature of an excellent light-fastness and are a novel class of fluorescence dyes. The high Stokes shift of the substances, which is 112 nm, for example, in the compound of the formula I in which $R_1$ and $R_2$ are 2,5-di-tert-butylphenyl and n and m are 0, and render the substances of interest for dye lasers or as signal colours or for security markings or fluorescence solar collectors, is also unexpected. The high Stokes shift is also of interest in analysis for fluorescence markings. On the one hand, the exciting light can be blocked out very efficiently with such dyes, and on the other hand the fluorescence of interfering contaminants (with a "normal" Stokes shift) can be blocked out, so that a high analytical sensitivity and, on the other hand, a stable interference-insensitive measurement value results.

An intense fluorescence is also found with compounds of the formula I in which $R_1$ and $R_2$ are voluminous alkyl groups. These substances can be employed in the same way as the o-substituted aryl derivatives defined above.

Finally, if the naphthalenelactamimides of the formula I are treated with large amounts of alkali, the lactam ring is split by hydrolysis to give the imide ring, and the corresponding salts result (which can also be isolated as intermediates in the synthesis described for compounds of the formula 1). However, this hydrolytic cleavage is fully reversible, and the lactam-imides of the formula I are obtained again in their entirety, for example, from hot ethanolic solution on acidification with concentrated hydrochloric acid or by heating with glacial acetic acid. Naphthalenelactamimides of the formula I which are of particular interest are those in which $R_1$ and $R_2$ are identical and are preferably a branched $C_3$–$C_{25}$alkyl group which is unsubstituted or substituted by phenyl, or a radical of the formula II, in which $R_3$ and $R_4$ are $C_1$–$C_{12}$alkyl and o is 0 or 1, but in particular those in which $R_1$ and $R_2$ are a radical of the formula II, where $R_3$ and $R_4$ independently of one another are methyl or tert-butyl, preferably 2-methylphenyl, 2,3-dimethylphenyl, 2-methyl-5-tert-butylphenyl, 2-tert-butylphenyl or 2,5-di-tert-butylphenyl, and in particular those in which $R_1$ and $R_2$ are 2-butyl, 2-methyl-2-butylhexyl, 2,2-dimethylheptyl, 2,2-dihexyloctyl, 1-ethylcyclohexylmethyl, 1-(n-propyl)-cyclohexylmethyl, 2-ethyl-2-phenylbutyl or 2-(n-butyl)-2-phenylhexyl.

Particularly preferred naphthalenelactamimides of the formula I are those in which $R_1$ and $R_2$ are —CH($R_8$)$_2$, where $R_8$ is straight-chain $C_1$–$C_{12}$alkyl, preferably n-hexyl, n-heptyl, n-octyl, n-nonyl or n-decyl, and in particular those in which A and B independently of one another are methyl, phenyl or halogen, preferably chlorine.

However, those naphthalene-lactam-imides of the formula I in which m and n are 0 are also preferred.

On the basis of their properties, the compounds according to the invention are suitable for a large number of uses.

Thus, for example, they can be employed as dyes or as pigments for mass colouring of plastics or paints. The invention therefore furthermore relates to mass-coloured high molecular weight organic material comprising a compound of the formula I or V, and to a process for mass dyeing of high molecular weight organic material using these compounds.

Suitable plastics are, for example, polyolefins, polyvinyl chloride, fluoropolymers, for example polyfluoroethylene, polytrifluorochloroethylene or tetrafluoroethylene/hexafluoropropylene copolymer, silicone resins, but in particular engineering plastics, for example polycarbonates, polyacrylates, polymethacrylates, polystyrene, ABS, polyesters, in particular polyalkylene terephthalates, such as polybutylene terephthalate (PBT) or polyethylene terephthalate (PET), polyamides, polyether-ketones or polyurethanes, individually or in mixtures. The colourants (dyes or pigments) are advantageously employed in a concentration of 0.01 to 10, preferably 0.01–5% by weight, based on the polymer.

Examples of polyolefins which can be coloured with the compounds according to the invention are high and low density polyethylene (HD-PE, LD-PE and LLD-PE), polyisobutylene and, in particular, polypropylene, as well as copolymers of polyolefins with, for example, polyethers, polyether-ketones or polyurethanes. Polypropylene is preferred.

Colouring is carried out by the customary processes, for example by mixing a compound according to the invention or a mixture or such compounds with the granules or powder of the plastic, without it having to be incorporated into a preparation beforehand, and extruding the mixture to fibres, films or granules. The latter can then be shaped to objects, for example by the injection moulding process.

The resulting colourings of red fluorescence have a high purity and high saturation and have the distinctive feature of good transparency and good stability, in particular to light.

The invention furthermore relates to the use of the compounds according to the invention in security printing, as fluorescent dyes for machine-readable markings, as laser dyes, and for the preparation of printing toners ("non-impact printing toners"), colour filters, organic photoreceptors, electroluminescent and photoluminescent elements, optical information storage media or solar collectors.

The following examples illustrate the invention.

EXAMPLES 1–13

Preparation Of The Naphthalenetetracarboxylic Acid Bisimides

Example 1
N,N'-di(2-butyl)naphthalene-1,8:4,5-bis(dicarboximide)

2.75 g (10.2 mmol) of naphthalene-1,8:4,5-tetracarboxylic bisanhydride are introduced into 150 ml of N,N-dimethylformamide, and 2.24 g (30.6 mmol) of 2-butylamine are added. The reaction mixture is heated at 170° C. for 24 hours. It is then stirred carefully into 400 ml of 2N HCl cooled to 0° C. During this operation, a flesh-coloured precipitate separates out. After the mixture has been stirred at room temperature for one hour, the dye crude product is separated off over a D4 glass filter frit, the pale yellow-coloured filtrate is discarded and the residue is dried at 110° C. for 8 hours. To remove unreacted edduct, the sand-coloured, fine powder is boiled up with 400 ml of saturated sodium carbonate solution, and the insoluble residue is separated off over a D4 glass filter frit and dried again at 110° C. for 8 hours. In the reaction in N,N'-dimethylformamide, small amounts of oily by-products which adhere firmly to the dye crude product and have to be removed before purification by column chromatography are obtained. For this, the resulting crude product is stirred three times in 100 ml of ethanol each time and filtered off. The filtrate is discarded. 3.82 g (99%) of dye crude product which has a pale pink colouration are obtained. The bisimide itself is colourless, and the colour impression results due to the N,N'-di(2-butyl)perylene-3,4:9,10-bis(dicarboximide) also formed in traces, which is identified as the sole impurity by thin layer chromatography. Removal of the traces of the perylenebisimide from the naphthalenebisimide is very difficult and is only poorly achieved even with the aid of column chromatography, since the $R_f$ values are very similar. Good separation results are achieved on silica gel using chloroform/glacial acetic acid in the ratio (39:1) as the mobile phase; separation is also possible with toluene. For analytical purity, the product had to be purified three times by column chromatography and then recrystallized by extraction from ethanol. Yield 3.82 g (99%)–melting point 192° C.–$R_f$(CHCl$_3$)=0.4–$R_f$(CHCl$_3$/glacial acetic acid (10:1)) =0.8. UV(CHCl$_3$):$\lambda_{max}$($\epsilon$)=381 (47910), 360 (39040), 343 (22930), 242 (50560).

$C_{46}H_{54}N_2O_4$ (698.9) Calculated C 69.83, H 5.86, N 7.40; Found C 69.97, H 5.93, N 7.07.

Example 2
N,N'-di(2-methyl-2-butylhexyl)naphthalene-1,8:4.5-bis(dicarboximide)

2.75 g (10.25 mmol) of naphthalene-1,8:4,5-tetracarboxylic bisanhydride are heated at boiling point with 4.38 g (30.6 mmol) of 2-methyl-2-propylhexylamine in 150 ml of N,N-dimethylformamide for 24 hours. The solution is cooled to room temperature overnight and 400 ml of 2N HCl are added. During this operation, the reaction product is obtained as a fine, beige precipitate. To bring the precipitation to completion, the mixture is stirred at room temperature for one hour. The reaction product is separated off from the reaction solution over a D4 glass filter frit. 4.9 g (92%) of a colourless powder are obtained. For purity according to elemental analysis, the product is purified by column chromatography on silica gel using chloroform/glacial acetic acid in the ratio 39:1. Yield 4.7 g (88%) of a colourless powder–melting point 225° C.–$R_f$(silica gel/CHCl$_3$)=0.29. –UV (CHCl$_3$)$\lambda_{max}$($\epsilon$)=380.7 nm (27660), 360.1 (23170), 342.0 (14650), 326.5 (9690).

$C_{32}H_{42}N_2O_4$ (518.7) Calculated C 74.10, H 8.10, N 5.40; Found C 74.16, H 8.04, N 5.58.

Example 3
N,N'-di(2,2-dimethylheptyl)naphthalene-1,8:4,5-bis(dicarboximide)

2.75 g (10.3 mmol) of naphthalene-1,8:4,5-tetracarboxylic bisanhydride are heated at the boiling point with 4.38 g (30.6 mmol) of 2,2-dimethylheptylamine in 60 ml of glacial acetic acid for 2.5 hours. The solution is cooled to room temperature overnight and 400 ml of 2N HCl are then added. During this operation, the reaction product is obtained as a fine, beige precipitate. To bring the precipitation to completion, the mixture is stirred at room temperature for one hour. The reaction product is separated off from the reaction solution over a D4 glass filter frit and dried at 110° C. for 8 hours. To remove unreacted bisanhydride, the crude product is boiled up twice in 200 ml of 10 percent potassium carbonate solution each time and the insoluble residue is separated off over a D-4 glass filter frit and dried at 110° C. for 8 hours. 2.4 g of crude product (45%, with an already very high purity) are obtained. For purification, the product is dissolved in boiling chloroform, small amounts of an insoluble, pale grey by-product (150 mg) are filtered off and ethanol is carefully added dropwise until crystallization starts. The mixture is left to stand overnight, and 1.04 g of fine, colourless small needles which are severely felted in one another and have a greasy effect are obtained as the first fraction. The filtrate is evaporated and the second fraction: 1.10 g, is obtained. For purity according to elemental analysis, the first fraction is purified by column chromatography on silica gel using chloroform as the mobile phase. Yield 1.90 g (37.5%) of a colourless powder–melting point 165° C.–$R_f$(CHCl$_3$)=0.59.–$R_f$(CHCl$_3$/glacial acetic acid 39:1)=0.61.–UV(CHCl$_3$): $\lambda_{max}$($\epsilon$)=381 (17160), 361 (16940), 344 (12100), 242 (23280), 327 (7180).

$C_{32}H_{42}N_2O_4$ (518.7) Calculated C 74.10, H 8.16, N 5.40; Found C 74.26, H 8.36, N 5.30.

Example 4
N,N'-di(2,2-dihexyloctyl)naphthalene-1,8:4,5-bis(dicarboximide)

2.75 g (10.3 mmol) of naphthalene-1,8:4,5-tetracarboxylic bisanhydride are heated at the boiling point with 9.11 g (30.6 mmol) of 2,2-dihexyloctylamine in 150 ml of N,N-dimethyl-formamide for 24 hours. The solution is cooled to room temperature overnight, during which the majority of the reaction product already precipitates out. The nonhomogeneous precipitate is filtered off, the filtrate is cooled to 0° C. and 400 ml of 2N HCl (0° C.) are added. During this operation, a small amount of product precipitates out and is combined with the main content of starting material. To remove unreacted bisanhydride, the crude product is boiled up once in 400 ml of 10 percent potassium carbonate solution, during which the reaction product melts because of its low melting point (about 50° C.). After the mixture has been cooled to 0° C., the reaction product solidifies and can be separated off over a D-4 glass filter frit, and is dried in vacuo over CaCl$_2$ for 8 hours. The crude product is dissolved in chloroform, a small amount of insoluble by-product (0.4 g) is filtered off and, for purity according to elemental analysis, the product is purified by column chromatography on silica gel using chloroform as the mobile phase. Yield 6.4 g (76%) of a colourless powder–melting point 77° C.–$R_f$(CHCl$_3$)=0.95.–$R_f$(CHCl$_3$/glacial acetic acid 39:1)=0.90.–UV(CHCl$_3$): $\lambda_{max}$($\epsilon$)=381 (29150), 361 (24440), 342 (14810), 327 (9550), 242 (31670).

$C_{54}H_{86}N_2O_4$ (827.3) Calculated C 78.40, H 10.48, N 3.39; Found C 77.79, H 10.18, N 3.61.

Example 5
N,N'-di(1-ethylcyclohexylmethyl)naphthalene-1,8:4,5-bis(dicarboximide)

2.75 g (10.2 mmol) of naphthalene-1,8:4,5-tetracarboxylic bisanhydride are suspended in 30 ml of glacial acetic acid, and 4.33 g (30.6 mmol) of 1-ethyl-1-aminomethylcyclohexane are added. After the reaction mixture has been heated at the boiling point for 15 minutes, it has become so viscous, because of the precipitate which has separated out, that thorough stirring is no longer possible. The reaction is interrupted, the reaction solution is cooled to room temperature and the precipitate is separated off over a D4 glass filter frit. After brief drying at 110° C., the sand-coloured powder is extracted by boiling with 300 ml of 10% potassium caronate solution, as a result of which residues of the anhydride are removed. After renewed drying, 8 hours at 110° C., 550 mg (10.5%) of a pale grey powder are isolated. To remove small amounts of by-products and last residues of edduct, column chromatography is carried out on silica gel using chloroform/glacial acetic acid (39:1) as the mobile phase. Yield 550 mg (10.5%). The highly purified product consists of colourless, tacky needles–melting point 256° C.–$R_f$(CHCl$_3$)=0.5.–$R_f$(CHCl$_3$/glacial acetic acid (10:1))=0.87.–UV(CHCl$_3$): $\lambda_{max}$ ($\epsilon$)=382 nm (22580), 361 (19090), 343 (11960) 326(7780), 241 (24380).

$C_{32}H_{38}N_2O_4$ (514.7) Calculated C 74.69, H 7.44, N 5.44; Found C 74.82, H 7.32, N 5.59.

Example 6
N,N'-di(1-n-propylcyclohexylmethyl)naphthalene-1,8:4,5-bis(dicarboximide)

2.75 g (10.2 mmol) of naphthalene-1,8:4,5-tetracarboxylic bisanhydride are suspended in 30 ml of glacial acetic acid, and 4.75 g (30.6 mmol) of 1-propyl-1-aminomethylcyclohexane are added. The reaction mixture is heated under reflux for 2 hours and the reaction is then interrupted by cooling to room temperature. 200 ml of 2N HCl are added. To bring the precipitation to completion, the mixture is stirred at room temperature for 1 hour. After brief drying at 110° C., the sand-coloured powder is extracted by boiling in 300 ml of 10 percent potassium carbonate solution, as a result of which residues of the anhydride are removed. After renewed drying, 8 hours at 110° C., 1.4 g (30%) of a colourless powder are isolated. To remove small amounts of by-products and last residues of edduct, column chromatography is carried out on silica gel using chloroform as the mobile phase and the product is recrystallized from chloroform/ethanol. Yield 780 mg (15%) of colourless, fine leaflets–melting point 227° C.–$R_f$(silica gel/CHCl$_3$)=0.80.

$C_{34}H_{42}N_2O_4$ (542.7) Calculated C 75.24, H 7.80, N 5.20; Found C 74.78, H 7.52, N 5.22.

Example 7
N,N'-di(2-ethyl-2-phenylbutyl)naphthalene-1,8:4,5-bis(dicarboximide)

2.75 g (10.3 mmol) of naphthalene-1,8:4,5-tetracarboxylic bisanhydride are introduced into 60 ml of glacial acetic acid, and 4.20 g (23.7 mmol) of 2-ethyl-2-phenylbutylamine are added. The reaction mixture is heated under reflux (oil bath temperature: 160° C.) for 2.5 hours. After cooling, the clear, brown-coloured reaction solution is stirred carefully into 400 ml of 2N hydrochloric acid (a small amount of beige powder which remains as a sediment in the reaction flask is suspended with a little distilled water and rinsed out). During this operation, a sand-coloured precipitate separates out and immediately aglutinates. After the mixture has been stirred at room temperature for one hour, the dye crude product is separated off over a D4 glass filter frit, the filtrate, which is coloured yellowish brown, is discarded and the residue is boiled up with 300 ml of 10 percent potassium carbonate solution in order to remove unreacted edduct. The insoluble residue is separated off over a D4 glass filter frit and dried over $CaCl_2$ for 8 hours. 190 mg (3.2%) of a cream-coloured powder are obtained. For preparation in analytical purity, purification by column chromatography on silica gel using chloroform as the mobile phase is sufficient. Extraction with ethanol as the solvent then gives the highly pure compound. Yield 80 mg (1.3%) –melting point 220° C.–$R_f(CHCl_3)$=0.38.–$R_f(CHCl_3$/glacial acetic acid 39:1)=0.57.–UV($CHCl_3$): $\lambda_{max}(\epsilon)$=381 (19800), 361 (19660), 345 (13740), 326 (82230), 240 (27990).

$C_{38}H_{38}N_2O_4$ (586.7) Calculated C 77.79, H 6.53, N 4.77; Found C 77.27, H 6.30, N 4.71.

Example 8

N,N'-di(2-n-butyl-2-phenylhexyl)naphthalene-1,8:4,5-bis(dicarboximide)

2.75 g (10.2 mmol) of naphthalene-1,8:4,5-tetracarboxylic bisanhydride are introduced into 150 ml of N,N-dimethylformamide, and 7.14 g (30.6 mmol) of 2-butyl-2-phenylhexylamine are added. The reaction mixture is heated at 170° C. for 24 hours. A colourless, flocculent precipitate is already formed in the orange-coloured reaction solution on cooling to room temperature. The mixture is stirred carefully into 400 ml of 2N hydrochloric acid cooled to 0° C. During this operation, a red, flocculent precipitate separates out. After the mixture has been stirred at room temperature for one hour, the dye crude product is separated off over a D4 glass filter frit, the pale yellow-coloured filtrate is discarded and the residue is dried at 110° C. for 8 hours. To remove unreacted edduct, the reddish brown, fine powder is boiled up with 400 ml of saturated sodium carbonate solution and the insoluble residue is separated off over a D4 glass filter frit and dried again at 110° C. for 8 hours. 6.05 g (85%) of dye crude product which has a pale pink colouration are obtained. The desired bisimide itself is colourless, the colour impression arising due to the N,N'-di(2-butyl-2-phenylhexyl)perylene-3,4:9,10-bis(dicarboximide) also formed in traces, which is identified as the sole impurity by thin layer chromatography. Removal of the perylenebisimide from the desired naphthalenebisimide is very difficult and is only poorly achieved even with the aid of column chromatography, since the $R_f$ values are very similar. The best separation results are achieved on silica gel using chloroform/glacial acetic acid in the ratio (39:1) as the mobile phase. Toluene also gives a good separation result, but the rate of migration is very low. For analytical purity, a small amount of product had to be purified three times by column chromatography. Extraction with ethanol as the solvent then gave the highly pure compound. Yield 6.0 g (84%); the analytically pure product consists of fine, colourless needles–melting point 162° C.–$R_f(CHCl_3)$=0.68.–$R_f(CHCl_3$/glacial acetic acid 39:1)= 0.66.–UV($CHCl_3$): $\lambda_{max}(\epsilon)$=381 (19690), 361 (19470), 343 (13760), 241 (31090), 327 (7180).

$C_{46}H_{54}N_2O_4$ (698.9) Calculated C 79.05, H 7.79, N 4.01; Found C 78.76, H 7.75, N 4.07.

Example 9

N,N'-di(2,3-di-methylphenyl)naphthalene-1,8:4,5-bis(dicarboximide)

1.02 g (3.80 mmol) of naphthalene-1,8:4,5-tetracarboxylic bisanhydride are heated at the boiling point with 1.37 g (11.31 mmol) of 2,3-dimethylaniline in 20 ml of glacial acetic acid for 1 hour, during which, after initial solution, a voluminous precipitate forms. The reaction solution is cooled and 200 ml of distilled water are added. The precipitate is separated off and boiled up twice in 200 ml of 10 percent potassium carbonate solution in order to remove unreacted bisanhydride. The reaction product is separated off over a D4 glass filter frit and dried at 110° C. for 8 hours. 1.74 g (97%) of crude product, the purity of which is already very high, are obtained. A portion of the crude product is dissolved in chloroform and, for purity according to elemental analysis, purified by column chromatography on silica gel using chloroform as the mobile phase. Yield 1.10 g (61%) of fine, yellow needles–melting point>350° C.–$R_f(CHCl_3)$=0.25.–$R_f(CHCl_3$/glacial acetic acid 39:1) =0.57.–UV($CHCl_3$): $\lambda_{max}(\epsilon)$=380 (26560), 360 (23940), 342 (14780), 327 (7430), 242 (30300).

$C_{30}H_{22}N_2O_4$ (474.5) Calculated C 75.94, H 4.67, N 5.90; Found C 75.61, H 4.63, N 5.76.

Example 10

N,N'-di(5-tert-butylphenyl-2-methyl)naphthalene-1,8:4,5-bis(dicarboximide)

2.75 g (10.3 mmol) of naphthalene-1,8:4,5-tetracarboxylic bisanhydride are heated at the boiling point with 5.00 g (30.6 mmol) of 2-tert-butyl-2-methylphenylamine in 20 ml of glacial acetic acid for 1 hour, during which, after initial solution, a voluminous precipitate forms. The reaction solution is cooled and 200 ml of distilled water are added. The precipitate is separated off and boiled up in two portions of 200 ml of 10 percent potassium carbonate solution in order to remove unreacted bisanhydride. The reaction product is separated off over a D4 glass filter frit and dried at 110° C. for 8 hours. 5.10 g (89%) of crude product, the purity of which is already very high, are obtained. A portion of the crude product is dissolved in chloroform and, for purity according to elemental analysis, is purified by column chromatography on silica gel using chloroform as the mobile phase. Yield 3.5 g (61%, extrapolated) of fine, yellow needles–melting point 318° C.–$R_f(CHCl_3)$=0.46.–$R_f(CHCl_3$/glacial acetic acid 39:1= 0.57.–UV($CHCl_3$): $\lambda_{max}(\epsilon)$=380 (27130), 360 (24410), 343 (14920), 326 (7460), 240 (36720).

$C_{36}H_{34}N_2O_4$ (558.7) Calculated C 77.40, H 6.13, N 5.01; Found C 77.69, H 6.11, N 5.20.

Example 11

N,N'-di(2-tert-butylphenyl)naphthalene-1,8:4,5-bis(dicarboximide) 2.75 g (10.3 mmol) of naphthalene-1,8:4, 5-tetracarboxylic bisanhydride are introduced into 20 ml of glacial acetic acid, and 4.57 g (30.6 mmol) of 2-tert-butylaniline are added. The reaction mixture is heated under reflux for 2 hours. After this reaction time, the mixture is cooled to room temperature and 400 ml of 2N HCl are added. The resulting precipitate is separated off over a porcelain suction filter and boiled up with 300 ml of 10 percent potassium carbonate solution in order to remove unreacted bisanhydride. The insoluble residue is separated off over a D4 glass filter frit and dried at 110° C. for 8 hours. 5.33 g (98%) of dye crude product are obtained. For analytical purity, the dye is purified by column chromatography on silica gel using chloroform, during which two fractions following one another closely, which are the two atropisomers, are obtained. Three fractions are taken off. From the resulting fractions, the chloroform is removed down to a few milliliters and the two products are precipitated by careful addition of ethanol. Yield 4.88 g (90%) of cis and trans in about equal amounts. Yields: mixed fraction of isomers I and II: 2.2 g (40.4%) of a colourless powder. Isomer I: 1.4 g (26%) of a colourless powder–melting point 332–338° C.–$R_f$($CHCl_3$)=0.30.–$R_f$($CHCl_3$/glacial acetic acid 39:1)=0.54.–UV($CHCl_3$): $\lambda_{max}(\epsilon)$=381 (28080), 360 (24290), 343 (14740), 326 (7580), 242 (26140).

$C_{34}H_{30}N_2O_4$ (530.6) Calculated C 79.96, H 5.70, N 5.28; Found C 77.34, H 5.86, N 4.98.

Isomer II: 1.28 g (23.5%) of colourless fine small needles–melting point 333° C.–$R_f$($CHCl_3$)=0.11.–$R_f$($CHCl_3$/glacial acetic acid 39:1)=0.54.–UV($CHCl_3$): $\lambda_{max}(\epsilon)$=381 (28220), 360 (24690), 342 (14880), 326 (7500), 241 (36560).

$C_{34}H_{30}N_2O_4$ (530.6) Calculated C 76.96, H 5.70, N 5.28; Found C 76.55, H 5.70, N 5.31.

Example 12

N,N'-di(2,5-di-tert-butylphenyl)naphthalene-1,8:4,5-bis(dicarboximide)

2.75 g (10.2 mmol) of naphthalene-1,8:4,5-tetracarboxylic bisanhydride are introduced into 150 ml of N,N-dimethylformamide, and 3.14 g (30.6 mmol) of 2,5-di-tert-butylaniline are added. The reaction mixture is heated at 170° C. for 24 hours. The mixture is stirred carefully into 400 ml of 2N hydrochloric acid, cooled to 0° C. During this operation, a sand-coloured precipitate separates out. After the mixture has been stirred at room temperature for one hour, the dye crude product is separated off over a D4 glass filter frit, the pale yellow-coloured filtrate is discarded and the residue is dried at 110° C. for 8 hours (8.3 g of an ochre-coloured powder). To remove unreacted edduct, the sand-coloured, fine powder is boiled up with 400 ml of saturated sodium carbonate solution and the insoluble residue is separated off over a D4 glass filter frit and dried again at 110° C. for 8 hours. In the reaction in N,N-dimethylformamide, small amounts of oily by-products which adhere firmly to the dye crude product and should be removed before purification by column chromatography are formed. For this, the crude product is stirred three times in 100 ml of ethanol each time and filtered off. The filtrate is discarded. 3.43 g (52%) of an ochre-coloured powder which has a pale reddish tinge is obtained. The desired bisimide itself is pale yellow, the colour impression resulting from the N,N'-di(2,5-di-tert-butyphenyl)perylene-3,4:9,10-bis(dicarboximide) also formed in traces, which is identified as the sole impurity by thin layer chromatography. Removal of the perylenebisimide from the desired naphthalenebisimide is very difficult and is only poorly achieved even with the aid of column chromatography, since the $R_f$ values are very similar. The best separation results are achieved on silica gel using chloroform/glacial acetic acid in the ratio (39:1) as the mobile phase. Toluene gives a similarly good separation result, although the rate of migration is very low. For analytical purity, a small amount of the product is purified three times by column chromatography. Extraction with ethanol as the solvent then gives the highly pure compound as pale yellow, fine small needles.–Melting point>250° C.–$R_f$($CHCl_3$)=0.73.–$R_f$($CHCl_3$/glacial acetic acid 39:1)= 0.69.–UV($CHCl_3$): $\lambda_{max}(\epsilon)$=381 (24980), 360 (22910), 343 (14890), 328 (8400), 242 (40110).

$C_{42}H_{46}N_2O_4$ (642.8) Calculated C 78.47, H 7.21, N 4.36; Found C 77.48, H 7.28, N 4.32.

Example 13

N,N'-di(2,5-di-tert-butylphenyl)naphthalene-1,8:4,5-bis(dicarboximide)

2.75 g (10.2 mmol) of naphthalene-1,8:4,5-tetracarboxylic bisanhydride are introduced into 60 ml of glacial acetic acid, and 4.17 g (40.6 mmol) of 2,5-di-tert-butylaniline are added. The reaction mixture is heated under reflux (oil bath temperature: 160° C.) for 2.0 hours and, after cooling, is stirred carefully into 400 ml of 2N hydrochloric acid. During this operation, a sand-coloured precipitate separates out. After the mixture has been stirred at room temperature for one hour, the dye crude product is separated off over a D4 glass filter frit, the filtrate, which is coloured yellowish brown is discarded and the residue is dried at 110° C. for 8 hours. Yield 8.3 g of an ochre-coloured powder. To remove unreacted edduct, the sand-coloured, fine powder is boiled up with 400 ml of 10 percent potassium carbonate solution and the insoluble residue is separated off over a D4 glass filter frit and dried again at 110° C. for 8 hours. 8.45 g of beige-coloured powder are obtained. For analytical purity, purification by column chromatography on silica gel using chloroform as the mobile phase is sufficient. Extraction with ethanol as the solvent then gives the compound in a highly pure form as pale yellow, fine small needles. Yield 3.43 g (52%)–melting point>250° C.–$R_f$($CHCl_3$)=0.73.–$R_f$($CHCl_3$/glacial acetic acid 39:1)=0.69.–UV($CHCl_3$): $\lambda_{max}(\epsilon)$=381 (24980), 360 (22910), 343 (14890), 328 (8400), 242 (40110).

$C_{42}H_{46}N_2O_4$ (642.8) Calculated C 78.47, H 7.21, N 4.36; Found C 77.48, H 7.28, N 4.32.

EXAMPLES 14–23

Preparation Of The Naphthalenelactamimides

Example 14

N,N'-di(2-tert-butylphenyl)-1-aminonaphthalene-4,5:8-tricarboxylic acid 1,8-lactam-4,5-imide 250 mg (0.50 mmol) of the N,N'-di(2-tert-butylphenyl)naphthalene-1,8:4,5-bis(dicarboximide) prepared according to Example 11 above are heated under reflux with 260 mg (3.94 mmol) of 85 percent potassium hydroxide (lozenges) in 40 ml of ethanol for 8 hours. The initially pale yellow solution changes colour via yellow to orange and finally to pale red. The reaction is monitored by UV/vis spectroscopy. After 8 hours, the bands characteristic for the edduct have disappeared completely and only the very broad absorption of the product, shifted to a long wavelength, is still present. The reaction solution is stirred into 200 ml of distilled water and diluted to 300 ml in total with distilled water, and 100 ml of concentrated HCl are added. During this operation, an intensely orange precipitate is obtained as the reaction product. To bring the precipitation to completion, the mixture is stirred at room temperature for one hour and left to stand overnight. The reaction product is separated off from the reaction solution via a D4 glass filter frit and dried at 110° C. for 8 hours. 300 mg of crude product are obtained. It can be seen from the thin layer chromatogram (silica gel/chloroform) that, in addition to the desired compound, a second reaction product is formed, which adsorbs firmly on the silica gel and remains at the start of the column. It is N,N'-di(2-tert-butylphenyl)-1-aminonaphthalene-4,5:8-tricarboxylic acid 4,5-imide, or the potassium salt of this compound with an open ring. The product is boiled up briefly with 100 ml of ethanol, 15 ml of concentrated HCl are added, the mixture is heated until the colour changes from pale red to yellowish orange and the solution is then cooled. After the product has been precipitated again with distilled water and the luminous orange precipitate has been separated off and dried, the product is boiled up with 200 ml of 10 percent potassium carbonate solution. The insoluble residue is separated off over a glass filter frit and, for purification in a highly pure form, is dissolved completely in chloroform and purified at least three times by column chromatography on silica gel using chloroform as the mobile phase. Yield 160 mg (67%) of a fine, yellowish orange powder–melting point 247° C.–$R_f$ (CHCl$_3$)=0.87. UV(CHCl$_3$): $\lambda_{max}(\epsilon)$=431.8 (7000), 361.7 (6330), 343.9 (5240), 314.2 (5780), 265.2 (21750).–fluorescence (CHCl$_3$): $\lambda_{max}$=544.5 nm.

$C_{33}H_{30}N_2O_4$ (502.6) Calculated C 78.86, H 6.02, N 5.57; Found C 78.29, H 5.92, N 5.36.

Example 14(a)

N,N'-di(2-tert-butylphenyl)-1-aminonaphthalene-4,5:8-tricarboxylic acid 4,5-imide potassium salt—intermediate in the ring-narrowing reaction 240 mg (0.47 mmol) of the N,N'-di(2-tert-butylphenyl) naphthalene-1,8:4,5-bis(dicarboximide) prepared according to Example 11 above are reacted with 700 mg (12.5 mmol) of 85 percent KOH in 10 ml of a DMSO/ethanol mixture (2:3) as described above. After a reaction time of three hours at 100° C., 100 ml of half-concentrated HCl are added dropwise to the still hot reaction mixture through the reflux condenser. During this operation, the potassium salt precipitates out in a luminous red-orange form. To bring the precipitate to completion, the mixture is stirred at room temperature for one hour, the precipitate is then filtered off with suction over a D4 glass filter frit, the clear filtrate is discarded and the residue is dried at 80° C. overnight. Yield 250 mg (96%) of an orange-red powder, highly electrostatic–$R_f$(CHCl$_3$)=0.05.–UV (CHCl$_3$): $\lambda_{max}(\epsilon)$=451.4 nm.–UV (EtOH): $\lambda_{max}(\epsilon)$=455.5 nm.–FAB-MS (70 eV): m/z (%)=519.2 (100) [M$^+$, $C_{33}H_{31}N_2O_4$], 520.2 (38), 475.2 (48) [M$^+$—CO$_2$], 476.2 (16).

Example 15

N,N'-di(2-tert-butylphenyl)-1-aminonaphthalene-4,5:8-tricarboxylic acid 1,8-lactam-4,5-imide—reaction with KOH in methanol/DMSO 250 mg (0.50 mmol) of the N,N'-di(2-tert-butylphenyl) naphthalene-1,8:4,5-bis(dicarboximide) prepared according to Example 11 above are heated under reflux with 700 mg (12.5 mmol) of 85 percent potassium hydroxide (lozenges) in 6 ml of methanol and 4 ml of dimethylsulfoxide for 4 hours. The initially pale yellow solution changes colour via yellow to orange and finally to pale red. 100 ml of half-concentrated hydrochloric acid are added to the reaction solution. During this operation, an intensely orange precipitate is obtained as the reaction product. To bring the precipitation to completion, the mixture is stirred at room temperature for one hour and left to stand overnight. The reaction product is separated off from the reaction solution via a D4 glass filter frit and dried at 110° C. for 8 hours. It can be seen from the thin layer chromatogram (silica gel/chloroform) that, in addition to the desired compound, a second reaction product which adsorbs firmly to the silica gel and remains at the start of the column is formed. This is N,N'-di(2-tert-butylphenyl)-1-aminonaphthalene-4,5:8-tricarboxylic acid 4,5-imide, or the potassium salt of this open-ring compound. The product is boiled up briefly with 100 ml of ethanol, 15 ml of concentrated HCl are added and the mixture is heated until the colour changes from pale red to yellowish orange. After the product has been precipitated again with distilled water and the luminous yellowish orange precipitate has been separated off and dried, the product is boiled up with 200 ml of 10 percent potassium carbonate solution and the insoluble residue is separated off over a glass filter frit and, for preparation in a highly pure form, is dissolved completely in chloroform and purified once by column chromatography on silica gel using chloroform as the mobile phase. Yield 190 mg (79%) of a fine, yellowish orange powder–melting point 247° C.–$R_f$(CHCl$_3$)=0.87.–UV(CHCl$_3$): $\lambda_{max}(\epsilon)$=431.8, 361.7, 343.9, 314.2, 265.2.–fluorescence (CHCl$_3$): $\lambda_{max}$=544.5 nm.–MS (70 eV): m/z (%)=502.2 (1) [M$^+$], 487.2 (2) [M$^+$—CH$_3$], 445.2 (100) [M$^+$—C(CH$_3$)$_3$].

Example 16

N,N'-di(2,5-di-tert-butylphenyl)-1-aminonaphthalene-4,5:8-tricarboxylic acid 1,8-lactam-4,5-imide—reaction with KOH in ethanol 290 mg (0.45 mmol) of the N,N'-di(2,5-di-tert-butylphenyl)naphthalene-1,8:4,5-bis(di-carboximide) obtained according to Example 12 above are boiled under reflux with 290 mg (4.39 mmol) of 85 percent potassium hydroxide (lozenges) in 40 ml of ethanol for 8 hours. The initially pale yellow solution changes colour via yellow to orange, reddish brown and, when the boiling point is reached, to brownish black. The reaction is monitored by UV/vis spectroscopy. After 8 hours, the bands characteristic of the edduct have disappeared completely and the very broad absorption of the product, shifted to a long wavelength, is present. The pale red reaction solution is stirred into 200 ml of distilled water and diluted to 300 ml in total with distilled water, and 100 ml of concentrated HCl are added. An intensive orange precipitate is obtained. To bring the precipitation to completion, the mixture is stirred at room temperature for one hour. The reaction product is separated off from the reaction solution over a D4 glass filter frit and dried at 110° C. for 8 hours. The product is boiled up with 100 ml of glacial acetic acid, precipitated again with distilled water, filtered off with suction and dried at 110° C. for 8 hours. It is then boiled up with 200 ml of 10 percent potassium carbonate solution, the insoluble residue is filtered off and, after renewed drying, the product is dissolved completely in chloroform and purified by column chromatography on silica gel using chloroform as the mobile phase. Yield 130 mg (47%) of a fine, orange powder–melting point 165–170° C. (product contaminated with bisimide)–$R_f$ (CHCl$_3$)=0.96.–UV(CHCl$_3$): $\lambda_{max}(\epsilon)$=433.6 (14410), 381.1 (14300), 362.1 (20920).–fluorescence (CHCl$_3$): $\lambda_{max}$=554.8 nm.

$C_{41}H_{46}N_2O_4$ (614.8) Calculated C 80.10, H 7.54, N 4.56; Found C 79.93, H 7.58, N 4.57.

Example 17

N,N'-di(2,5-di-tert-butylphenyl)-1-aminonaphthalene-4,5:8-tricarboxylic acid 1,8-lactam-4,5-imide- reaction with KOH in methanol/dimethylsulfoxide (a) N,N'-Di(2,5-di-tert-butylphenyl)-1-aminonaphthalene-4,5:8-tricarboxylic acid 4,5-imide potassium salt:

–590 mg (0.90 mmol) of the N,N'-di(2,5-di-tert-butylphenyl)-naphthalene-1,8:4,5-bis(dicarboximide) prepared according to Example 12 above are heated at 100° C. with 1.4 g (25 mmol) of 85 percent potassium hydroxide (lozenges) in 8 ml of methanol and 6 ml of dimethylsulfoxide for 3 hours. The initially pale yellow solution changes colour via yellow to orange, reddish brown and, when the boiling point is reached, to brownish black. 100 ml of half-concentrated HCl are added to the solution, which is pale red at the end of the reaction time. An intensively orange precipitate is obtained. To bring the precipitation to completion, the mixture is stirred at room temperature for one hour. The reaction product is separated off from the reaction solution via a D4 glass filter frit and dried at 110° C. for 8 hours. Yield 560 mg of yellowish orange powder.–MS(-FAB/70 eV): m/z (%)=632.2 (61 [M$^+$+1], 631.2 (100) [M$^+$-2], 588.3 (20) [M$^+$—CO$_2$], 587.3 (46).

(b) N,N'-Di(2,5-di-tert-butylphenyl)-1-aminonaphthalene-4,5:8-tricarboxylic acid 4,5-imide:

–500 mg of N,N'-di(2,5-di-tert-butylphenyl)-1-aminonaphthalene-4,5:8-tricarboxylic acid 4,5-imide potassium salt are boiled up with 50 ml of glacial acetic acid, precipitated again with 400 ml of distilled water, filtered off with suction and dried at 110° C. for 8 hours. 410 mg of red, finely crystalline powder are obtained. MS(-FAB/70 eV): m/z (%)=634.2 (41) [M$^+$+1], 633.2 (100) [M$^+$], 632.2 (62), 577.1 (23) [M$^+$+1–C(CH$_3$)$_3$], 576.2 (16) [M$^+$—C(CH$_3$)$_3$], 575.2 (39).

(c) N,N'-Di(2,5-di-tert-butylphenyl)-1-aminonaphthalene-4,5:8-tricarboxylic acid 1,8-lactam-4,5-imide:

–200 mg (0.32 mmol) of N,N'-di(2,5-di-tert-butylphenyl)-1-aminonaphthalene-4,5:8-tricarboxylic acid 4,5-imide are heated to the boiling point in 100 ml of ethanol, 15 ml of of concentrated HCl are added and heating is continued until the change in colour from pale red to yellowish orange has taken place. 300 ml of distilled water are added to the solution and the mixture is stirred at room temperature for 1 hour and left to stand overnight. The yellowish orange precipitate is filtered off with suction over a glass filter frit (D5), dried at 110° C. for 8 hours and chromatographed on activated silica gel (activity II, 10% by weight of distilled H$_2$O) using chloroform. Yield 150 mg (79%) of a fine yellowish orange powder. Yield calculated for the entire batch 340 mg (62%)–melting point 275° C.–R$_f$(CHCl$_3$)= 0.96.–UV(CHCl$_3$): $\lambda_{max}(\epsilon)$=432.5 (7970), 361.9 (7450).–fluorescence (CHCl$_3$): $\lambda_{max}$=554.8 nm.

C$_{41}$H$_{46}$N$_2$O$_3$ (614.8) Calculated C 80.10, H 7.54, N 4.56; Found C 79.93 H 7.58, N 4.57.

Example 18

N,N'-Di(2-methyl-5-tert-butylphenyl)-1-aminonaphthalene-4,5:8-tricarboxylic acid 1,8-lactam-4,5-imide 190 mg (0.34 mmol) of the N,N'-di(2-methyl-5-tert-butylphenyl)naphthalene-1,8:4,5-bis(dicarboximide) prepared according to Example 10 above are heated under reflux with 190 mg (2.88 mmol) of 85 percent potassium hydroxide (lozenges) in 40 ml of ethanol for 8 hours. The initially pale yellow solution changes colour via yellow to orange, reddish brown and, when the boiling point is reached, to brownish black. The reaction can be monitored by UV/vis spectroscopy. After 8 hours, the bands characteristic of the edduct have disappeared completely and only the very broad absorption of the product, shifted to a long wavelength, is still present. The yellowish brown solution is stirred into 200 ml of distilled water and diluted to 300 ml in total with distilled water and 100 ml of concentrated HCl are added. During this operation, the reaction product is obtained as an orange precipitate. To bring the precipitation to completion, the mixture is stirred at room temperature for one hour. The reaction product is filtered off with suction over a D4 glass filter frit and dried at 110° C. for 8 hours. The resulting red powder is boiled up with 20 ml of glacial acetic acid, 200 ml of distilled water are added again and the mixture is neutralized with potassium hydroxide. During this operation, a flocculent, yellow precipitate is formed, which is filtered off with suction and dried at 110° C. for 8 hours. Crude product: yield 150 mg of a fine, yellow powder. The product is dissolved completely in chloroform and purified by column chromatography over silica gel using chloroform as the mobile phase. Yield 130 mg (68%) of a fine, orange powder–melting point 211° C.–R$_f$(CHCl$_3$)= 0.88.–UV(CHCl$_3$): $\lambda_{max}(\epsilon)$=432.2 (7350), 361.1 (6790), 343.4 (5720), 310.2 (6550), 264.7 (22790).–fluorescence (CHCl$_3$): $\lambda_{max}$=559.3 nm.

C$_{35}$H$_{34}$N$_2$O$_3$ (530.7) Calculated C 79.22, H 6.46, N 5.28; Found C 76.87, H 6.27, N 5.36.

Example 19

N,N'-Di(2-methyl-5-tert-butylphenyl)-1-aminonaphthalene 4,5:8-tricarboxylic acid 1.8-lactam-4,5-imide 190 mg (0.34 mmol) of the N,N'-di(2-methyl-5-tert-butylphenyl)naphthalene-1,8:4,5-tetracarboxylic acid bis (dicarboximide) prepared according to Example 10 above are heated at 100° C. with 700 mg (12.5 mmol) of 85 percent potassium hydroxide (lozenges) in 6 ml of methanol and 4 ml of dimethylsulfoxide for 3 hours. The initially pale yellow solution changes colour via yellow to orange, reddish brown and, when the boiling point is reached, to brownish black. The solution, which is pale red at the end of the reaction time, is stirred into 200 ml of distilled water and diluted to 300 ml in total with distilled water, and 100 ml of concentrated HCl are added. During this operation, the reaction product is obtained as an orange precipitate. To bring the precipitation to completion, the mixture is stirred at room temperature for one hour. The reaction product is filtered off with suction over a D4 glass filter frit and dried at 110° C. for 8 hours. The resulting red powder is dissolved in 100 ml of ethanol, 15 ml of concentrated HCl are added and the mixture is heated to the boiling point until the colour changes from pale red to yellowish orange. After addition of 400 ml of distilled water, a flocculent, yellow precipitate is formed, which is filtered off with suction and dried at 110° C. for 8 hours. The product is dissolved completely in chloroform and purified by column chromatography on activated silica gel (activity 11, 10% by weight of H$_2$O) using chloroform as the mobile phase. Yield 170 mg (89%) of a fine orange powder–melting point 211° C.–R$_f$(CHCl$_3$) =0.88.–UV(CHCl$_3$): $\lambda_{max}(\epsilon)$=432.2 (7350), 361.1 (6790), 343.4 (5720), 310.2 (6550), 264.7 (22790).–fluorescence (CHCl$_3$): $\lambda_{max}$=559.3 nm.

C$_{35}$H$_{34}$N$_2$O$_3$ (530.7) Calculated C 79.22, H 6.46, N 5.28; Found C 76.87, H 6.27, N 5.36.

Example 20

N,N'-Di(1-n-propylcyclohexylmethyl)-1-aminonaphthalene-4,5:8-tricarboxylic acid 1.8-lactam-4,5-imide 270 mg (0.45 mmol) of the N,N'-di(1-cyclohexyl-1-propylmethyl)naphthalene-1,8:4,5-tetracarboxylic acid bis (dicarboximide) prepared according to Example 6 are heated under reflux with 290 mg (4.39 mmol) of 85 percent potassium hydroxide lozenges in 40 ml of ethanol for 18 hours. The initially pale yellow solution changes colour via yellow to orange, reddish brown and, when the boiling point is reached, to brownish black. The reaction can be monitored by UV/vis spectroscopy. After 18 hours, the bands characteristic of the edduct disappeared completely, and only the very broad absorption of the product, shifted to a long wavelength, is still present. The pale red reaction solution is stirred into 200 ml of distilled water and diluted to 300 ml in total with distilled water, and 100 ml of concentrated HCl are added. During this operation, the reaction product is obtained as a deep orange precipitate. To bring the precipitation to completion, the mixture is stirred at room temperature for one hour. The reaction product is separated off from the reaction solution via a D4 glass filter frit and dried at 110° C. for 8 hours. The product is boiled up with 100 ml of glacial acetic acid, precipitated again with distilled water, filtered off with suction and dried at 110° C. for 8 hours. The product is dissolved completely in chloroform and purified several times by column chromatography on silica gel using chloroform as the mobile phase. Yield 25 mg (10%) of a fine, yellowish orange powder (still comprises small amounts of bisimide)–melting point 187°–191 ° C.–$R_f$(CHCl$_3$)=0.91.–UV(CHCl$_3$): $\lambda_{max}$=435.7, 381.6, 361.9, 342.4, 316.7, Sh 268.4.–fluorescence (CHCl$_3$): $\lambda_{max}$=541.5 nm.–MS (70 eV): m/z (%)=514.3 (100) [M$^+$], 497.3 (9) [M$^+$—OH], 390.2 (39) [M$^+$—C$_9$H$_{16}$], 266.1 (62) [M$^+$—C$_9$H$_{16}$].

Example 21
N,N'-Di(2,2-dimethylheptyl)-1-aminonaphthalene-4,5:8-tricarboxylic acid 1,8-lactam-4,5-imide 270 mg (0.45 mmol) of the N,N'-di(2,2-dimethylheptyl)naphthalene-1,8:4,5-bis(dicarboximide) prepared according to Example 3 above are heated under reflux with 290 mg (4.39 mmol) of 85 percent potassium hydroxide lozenges in 40 ml of ethanol for 8 hours. The initially pale yellow solution changes colour via yellow to orange, reddish brown and, when the boiling point is reached, to brownish black. The reaction can be monitored by UV/vis spectroscopy. After 8 hours, the bands characteristic of the edduct have disappeared completely and only the very broad absorption of the product, shifted to a long wavelength, is still present. The pale red reaction solution is stirred into 200 ml of distilled water and diluted to 300 ml in total with distilled water, and 100 ml of concentrated HCl are added. During this operation, the reaction product is obtained as a deep orange precipitate. To bring the precipitation to completion, the mixture is stirred at room temperature for one hour. The reaction product is separated off from the reaction solution over a D4 glass filter frit and dried at 110° C. for 8 hours. The product is boiled up with 100 ml of glacial acetic acid, precipitated again with distilled water, filtered off with suction and dried at 110° C. for 8 hours. The product is dissolved completely in chloroform and purified by column chromatography on silica gel using chloroform as the mobile phase. Yield 22 mg (8%) of a fine, orange powder (still contains low amounts of bisimide)–melting point 94° C.–$R_f$(CHCl$_3$)=0.89.–UV(CHCl$_3$): $\lambda_{max}(\epsilon)$=439.0 (6220), 361.8 (5170), 343.4 (5480), 328.0 (6380), 311.7 (6790), 267.8 (21320).–fluorescence (CHCl$_3$): $\lambda_{max}$=551.0 nm.–MS (70 eV): m/z (%)=490.3 (100) [M$^+$], 473.4 (5) [M$^+$—OH], 377.2 (29) [M$^+$—C$_8$H$_{16}$], 265.1 () [377.2–C$_8$H$_{16}$], 250.0 (1), 235.0 (1).

Example 22
N,N'-Di(2,2-dimethylheptyl)-1-aminonaphthalene-4,5:8-tricarboxylic acid 1,8-lactam-4,5-imide—reaction with KOH in methanol/dimethylsulfoxide 260 mg (0.5 mmol) of the N,N'-di(2,2-dimethylheptyl)naphthalene-1,8:4,5-tetracarboxylic acid bis(dicarboximide) prepared according to Example 3 above are heated at the boiling point with 700 mg (12.5 mmol) of 85 percent potassium hydroxide lozenges in a mixture of 4 ml of DMSO and 6 ml of methanol for 3 hours. The initially pale yellow solution changes colour via yellow to orange, reddish brown and, when the boiling point is reached, to pale red. The pale red reaction solution is stirred into 200 ml of distilled water and diluted to 300 ml in total with distilled water, and 100 ml of concentrated HCl are added. During this operation, the reaction product is obtained as a deep orange precipitate. To bring the precipitation to completion, the mixture is stirred at room temperature for one hour and left to stand overnight. The yellowish orange reaction product is filtered off with suction over a D4 glass filter frit and dried at 80° C. for 8 hours (caution: the crude product melts below 100° C.). The product is dissolved completely in chloroform and purified by column chromatography on silica gel (fine) using chloroform as the mobile phase. After removal of the solvent, 50 mg (20%) of a yellow powder are obtained, which is recrystallized from ethanol/water. Yield 45 mg (18%) of fine, yellow powder–melting point 97° C.–$R_f$(CHCl$_3$)=0.89.–UV(CHCl$_3$): $\lambda_{max}(\epsilon)$=439.0 (6220), 361.8 (5170), 343.4 (5480), 328.0 (6380), 311.7 (6790), 267.8 (21320).–fluorescence (CHCl$_3$): $\lambda_{max}$=551.0 nm.–MS (70 eV): m/z (%)=490.3 (100) [M$^+$], 473.4 (5) [M$^+$—OH], 377.2 (29) [M$^+$—C$_8$H$_{16}$], 265.1 [377.2–C$_8$H$_{16}$], 250.0 (1), 235.0 (1).

Example 23
Reaction of N,N'-di(2-tert-butylphenyl)naphthalene-1,8:4,5-bis(dicarboximide) to give the lactam-imide—with exclusion of O$_2$ 200 mg (0.38 mmol) of the bis(dicarboximide) prepared according to Example 11 above are suspended with 200 mg of 85 percent KOH and 20 ml of ethanol in a flask filled with argon and the suspension is heated at the boiling point in a stream of N$_2$ for 3 hours. During this operation, several changes in colour of the reaction mixture are observed: from yellow to yellowish brown via brown to reddish violet. At the end of the reaction time, 200 ml of distilled water (change in colour to yellowish orange) and 100 ml of concentrated HCl are added and the mixture is stirred at room temperature for 1 hour. It is left to stand overnight and the resulting yellow precipitate is separated off over a D4 glass filter frit and dried at 110° C. for 2 hours. The crude product (170 mg of a yellowish orange powder) is boiled up twice with 200 ml of 10% potassium carbonate solution each time. The insoluble residue (125 mg of a yellow powder: mixture A) is separated off and the yellow-coloured filtrate is neutralized carefully with concentrated HCl. The product which has precipitated out of the alkaline filtrate is also separated off and dried. 45 mg of an orange powder (mixture B) are obtained. The two crude products are analyzed by NMR and mass spectroscopy.

Two components can be detected in mixture A by mass spectroscopy, the mixture comprising the desired lactam, in addition to unreacted edduct. Mixture B comprises three compounds, edduct, lactam and the product of partial hydrolysis, N-(2-tert-butylphenyl)naphthalene- 1,8:4,5-tetracarboxylic acid 1,8-imide-4,5-anhydride. The amounts of the components contained in the two crude products can be estimated roughly from the $^1$H-NMR spectra of the crude products. The unreacted edduct gives a singlet at 8.85 ppm for the four hydrogen atoms of the naphthalene base skeleton, while for the lactam, four different doublets are found at 8.70, 8.43, 8.31 and 6.75 ppm, each corresponding to a hydrogen atom, and two doublets at 8.62 and 7.87 ppm correspond to the hydrolysis product (N-(2-tert-butylphenyl) naphthalene-1,8:4,5-tetracarboxylic acid 1,8-imide-4,5-anhydride).

Mixture A (125 mg):
60% edduct: 40% lactam.–MS (70 eV): m/z (%)=530.2 (0.5) [M$^+$, edduct], 515.2 (4) [M$^+$—CH$_3$, edduct], 473.1 (100) [M$^+$—C(CH$_3$)$_3$, edduct], 445.1 (84) [M$^+$—C(CH$_3$)$_3$, lactam], 416.1 (8) [473-C(CH$_3$)$_3$, edduct], 342.0 (30) [M$^+$—C(CH$_3$)$_3$, monoimide-monoanhydride].

Mixture B (45 mg):
47% edduct: 29% lactam: 24% monoimide-monoanhydride.–MS (70 eV): m/z (%)=530.2 (0.5) [M$^+$, edduct], 515.2 (2) [M$^+$—CH$_3$, edduct], 473.1 (56) [M$^+$—C(CH$_3$)$_3$, edduct], 463.1 (10), 445.1 (56) [M$^+$—C(CH$_3$)$_3$, lactam], 416.1 (9) [473-C(CH$_3$)$_3$, edduct], 384.1 (6), 371.1 (15), 366.1 (10), 356.1 (9), 354.1 (8), 342.0 (100) [M$^+$—C(CH$_3$)$_3$, monoimide-monoanhydride], 338.1 (8).

The following yields of the components of the two mixtures are obtained:

10 mg (50%) of N,N'-di(2-tert-butylphenyl)naphthalene-1,8:4,5-bis(dicarboximide) (starting material)

60 mg (31%) of N-(2-tert-butylphenyl)-1-aminonaphthalene 8:4,5-tricarboxylic acid 1,8-lactam-4,5-imide 10 mg (6.6%) of N-(2-tert-butylphenyl)naphthalene-1,8:4,5-tetracarboxylic acid 1,8-imide-4,5-anhydride (partial hydrolysis).

What is claimed is:

1. A naphthalenelactamimide of the formula I (I)

$R_1$ and $R_2$ independently of one another are $C_3$–$C_{10}$ cycloalkyl or a radical of the formula II to IV (II)

(III)

(IV)

A and B independently of one another are $C_1$–$C_6$alkyl, $C_3$–$C_6$cycloalkyl, $C_6$–$C_{10}$aryl, halogen, cyano, nitro, —$OR_6$, —$COR_6$, —$COOR_6$, —$OCOR_6$, —$CONR_6R_7$, —$OCONR_6R_7$, —$NR_6R_7$, —$NR_6COR_7$, —$NR_6COOR_7$, —$NR_6SO_2R_7$, —$SO_2R_7$, —$SO_3R_7$, —$SO_2NR_6R_7$ or —N=N—$R_6$, $R_3$ to $R_5$ independently of one another are halogen, $C_1$–$C_{12}$alkyl, phenyl or tolyl, where one $R_5$ can also be hydrogen, $R_6$ and $R_7$ independently of one another are $C_1$–$C_4$alkyl, phenyl or 4-tolyl, n and m independently of one another are 0, 1 or 2, o is an integer from 0 to 4, p is an integer from 0 to 3 and q is 0 or 1 with the proviso that $R_1$ and $R_2$ are not unsubstituted phenyl, methyl- or ethyl-substituted phenyl.

2. A naphthalenelactamimide according to claim 1, in which $R_1$ and $R_2$ are each independently a radical of the formula II to IV (II)

(III)

(IV)

A and B independently of one another are $C_1$–$C_6$alkyl, $C_3$–$C_6$cycloalkyl, $C_6$–$C_{10}$aryl, halogen, cyano, nitro, —$OR_6$, $COR_6$, —$OCOR_6$, —$CONR_6R_7$, —$OCONR_6R_7$, —$NR_6R_7$, —$NR_6COR_7$, —$NR_6COOR_7$, —$NR_6SO_2R_7$, —$SO_2R_7$, —$SO_3R_7$, —$SO_2NR_6R_7$ or —N=N—$R_6$, $R_3$ to $R_5$ independently of one another are halogen, $C_1$–$C_{12}$alkyl, phenyl or tolyl, where one $R_5$ can also be hydrogen, $R_6$ and $R_7$ independently of one another are $C_1$–$C_4$alkyl, phenyl or 4-tolyl, n and m independently of one another are 0, 1 or 2, o is an integer from 0 to 4, p is an integer from 0 to 3 and q is 0 or 1 with the proviso that, if $R_1$ or $R_2$ is a radical of formula II and o is 0, $R_3$ is halogen $C_3$–$C_{12}$alkyl, phenyl or tolyl.

3. A naphthalenelactamimide according to claim 2 in which $R_1$ and $R_2$ are each independently tert-butyl, 2-methyl-5-tert-butylphenyl-, 2-tert-butylphenyl, 2,3-di-tert-butylphenyl or 2,5-di-tert-butylphenyl.

4. A naphthalenelactamimide according to claim 1, in which $R_1$ and $R_2$ are each independently 1-ethylcyclohexylmethyl, 1-(n-propyl)-cyclohexylmethyl, 2-ethyl-2-phenylbutyl or 2-(n-butyl)-2-phenylhexyl.

5. A naphthalenelactamimide according to claim 1, in which A and B independently of one another are methyl, phenyl or halogen.

6. A naphthalenelactamimide according to claim 1, in which m and n are 0.

* * * * *